United States Patent [19]

Kobayashi et al.

[11] Patent Number: 4,902,807

[45] Date of Patent: Feb. 20, 1990

[54] PROCESS FOR BATCHWISE ACETAL PRODUCTION

[75] Inventors: Toshiaki Kobayashi, Nara; Kango Kujitani, Uji, both of Japan

[73] Assignee: New Japan Chemical Co., Ltd., Japan

[21] Appl. No.: 279,507

[22] Filed: Dec. 5, 1988

[30] Foreign Application Priority Data

Dec. 7, 1987 [JP] Japan .................. 62-310342

[51] Int. Cl.$^4$ .................................. C07D 319/04
[52] U.S. Cl. .................................... 549/364
[58] Field of Search ........................ 549/364

[56] References Cited

U.S. PATENT DOCUMENTS 3,721,682  3/1973  Murai et al. .............. 549/364
4,429,140  1/1984  Murai et al. .............. 549/370

Primary Examiner—Nicky Chan
Attorney, Agent, or Firm—Larson and Taylor

[57] ABSTRACT

Disclosed is a process for batchwise production of a 1,3:2,4-dibenzylidene-sorbitol or xylitor compound comprising subjecting a sorbitol or xylitol and a benzaldehyde compound to a condensation reaction in a reactor by feeding a homogeneous solution or suspension formed from (a) sorbitol or xylitor, (b) an aldehyde compound, (c) a lower alcohol, and if necessary (d) an acid catalyst, to the reactor, together with a hydrophobic organic solvent, continuously or intermittently while adjusting the rate of feeding of said homogeneous solution or suspension such that sorbitol or xylitol and the benzaldehyde compound are fed to the reaction system in a total amount per hour of about 0.1 to about 2 parts by weight per part by weight of the 1,3:2,4-dibenzylidene compound as found in the reaction system.

15 Claims, No Drawings

PROCESS FOR BATCHWISE ACETAL PRODUCTION

This invention relates to a commercially advantageous process for producing acetals.

Benzylidenesorbitols, which are a kind of acetals, are substances having unique properties and have a wide variety of uses. Thus, for example, they are useful as transparency improving agents for polypropylene and other resins, as flowability improving agents for paints, ink, adhesives and other compositions, and as solidifying agents for adhesives, cosmetics, pharmaceuticals and so forth.

Benzylidenesorbitols, benzylidenexylitols and like acetals, in particular 1,3:2,4-dibenzylidenesorbitol and the like 1,3:2,4-disubstituted compounds, are produced by condensation of a benzaldehyde with a polyhydric alcohol, such as sorbitol or xylitol, in the presence of an acid catalyst.

The present inventors have already proposed some processes for the production of such acetals, in particular 1,3:2,4-disubstituted forms. When evaluated comprehensively as a commercial production process, however, each of the processes proposed still has some or other problems.

For instance, in the process which comprises carrying out the reaction in a cyclohexane-containing reaction system in the form of a slurry in a reactor equipped with a usual impeller mixer (U.S. Pat. No. 3,721,682), the mixer becomes loaded excessively and stirring becomes difficult during the reaction, failing to give homogeneous product when the total concentration of the polyhydric alcohol having 5 or more hydroxyl groups and the benzaldehyde exceeds about 15% by weight. As a result, the production per lot can hardly be increased.

In the process proposed to overcome the above difficulties and described in U. S. Pat. No. 4,429,140, which comprises carrying out the reaction in increased reactant concentrations in the presence of an acid catalyst, a hydrophobic organic solvent (e.g. cyclohexane) and a water-soluble polar organic solvent (e.g. a lower alcohol) with forced agitation by means of a device capable of producing a kneading or crushing effect (said process being hereinafter referred to as "high concentration process"), there is a tendency toward formation of a highly hard gel during agitation of the reaction mixture slurry, which will lead to a decreased product yield and/or a decreased product quality if the intensity of agitation is insufficient. This is presumably due to changes in state of the reaction mixture from the flowable slurry, to paste and eventually to a substantially nonflowable gel with the progress of the reaction. The gel, when mechanically kneaded or crushed, eventually becomes crystalline (solid), giving the desired acetal of high purity. However, it appears that some gel remains as finely divided hard gel particles. The acid catalyst contained in such hard gel particles can hardly be neutralized or washed away with water. The dried product tends to have unsatisfactory heat stability presumably due to the residual acid catalyst.

Accordingly, it is an object of the invention to provide an industrially advantageous acetal production process which can overcome the above-mentioned drawbacks of the prior art processes.

The present invention provides a process for batchwise production of acetals of the general formula

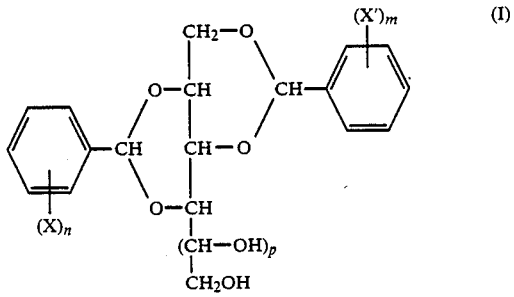

wherein X and X' are the same or different and each represent a hydrogen or halogen atom, an alkyl or alkoxy group containing 1 to 4 carbon atoms or a carboxyl group, m and n each represent an integer of 1 to 5 and p is 0 (zero) or 1, which comprises subjecting (a) a polyhydric alcohol of the general formula

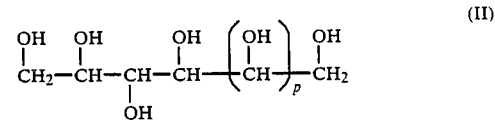

wherein p is as defined above, and (b) a benzaldehyde compound of the general formula

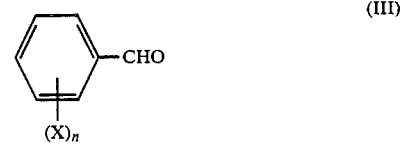

wherein X and n are as defined above, or a benzaldehyde compound of the general formula

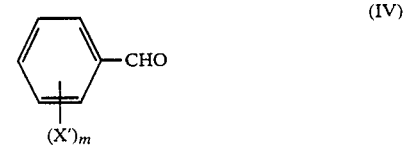

wherein X' and m are as defined above, or a mixture of said compound of general formula (III) and said compound of general formula (IV), to condensation reaction in a reactor by feeding a homogeneous solution or suspension formed from
(a) said polyhydric alcohol of general formula (II),
(b) said compound of general formula (III) or (IV) or said mixture,
(c) a lower alcohol and, if necessary,
(d) an acid catalyst,
to the reactor, together with a hydrophobic organic solvent, continuously or intermittently while adjusting the rate of feeding of said homogeneous solution or suspension such that said polyhydric alcohol of general formula (II) and said compound of general formula (III) or (IV) or said mixture are fed to the reaction system in a total amount per hour of about 0.1 to about 2 parts by weight per part by weight of the acetal of general formula (I) existing in the reaction system.

The present inventors made intensive investigations in an attempt to improve the prior art high concentration process and establish a commercial process for producing benzylidenesorbitols and, as a result, found that rapid changes in state, in particular gelation, of the reaction mixture and formation of hard gel particles within the reaction system can be avoided when the reactants are fed to the reaction system continuously or intermittently at a feeding rate within a specific range, not all at once as in the prior art processes. The present invention has been completed on the basis of this finding.

In accordance with the present invention, rapid changes in state of the reaction mixture within the reaction system can be avoided by feeding the reactants not all at once but continuously or intermittently with the progress of the reaction and therefore the desired acetals can be produced in good yields and with high selectivities. Furthermore, since the amount of reactants to be fed can be increased progressively or exponentially as the reaction proceeds, the desired acetal of the formula (I) can be efficiently produced.

The actals producible by the process according to the invention are of the general formula (I) shown hereinabove and include symmetrical compounds in which the two aromatic rings have the same number of the same substituents and nonsymmetrical compounds in which the two aromatic rings differ from each other in the number and kind of substituents and further include mixtures of such symmetrical compounds and/or nonsymmetrical compounds in any desired proportions.

The polyhydric alcohol of general formula (II), one of the starting materials in the production process according to the invention, is sorbitol or xylitol, or a mixture of sorbitol and xylitol in any desired proportions.

As the benzaldehyde compound of general formula (III) or (IV), the other starting material, there may be mentioned, among others, benzaldehyde, substituted benzaldehydes having 1 to 5, in particular 1 to 3, substituents selected from the class consisting of an alkyl group of 1 to 4 carbon atoms, a halogen atom, an alkoxy group of 1 to 4 carbon atoms and a carboxyl group, and mixtures of these in any desired proportions.

Preferred examples of the substituents on the benzene ring are p-methyl, p-ethyl, p-isopropyl, p-butyl, 2,4-dimethyl, 2,4,5-trimethyl, p-chloro, m-methyl, o-methyl, p-methoxy and p-fluoro.

The lower alcohol to be used in accordance with the invention is, for example, a saturated aliphatic alcohol of 1 to 4 carbon atoms, such as methanol, ethanol, propanol, isopropanol or butanol.

Any of usual Brønsted acids and Lewis acids may be used as the acid catalyst. More specifically, mention may be made of sulfuric acid, phosphoric acid, hydrochloric acid, p-toluenesulfonic acid, $C_{2-12}$ alkyl-substituted benzenesulfonic acid, G acid and R acid, zinc chloride, among others.

In the practice of the invention, the above-mentioned polyhydric alcohol and benzaldehyde compound (hereinafter collectively referred to as "substrates") are mixed with the lower alcohol to give a homogeneous solution or suspension. This homogeneous solution or suspension may contain the above-mentioned acid catalyst. Generally, the polyhydric alcohol of general formula (II) and the benzaldehyde compound of general formula (III) or (IV), when mixed together, do not form a homogeneous solution but form a mixture composed of two layers. However, when the lower alcohol is added to this mixture, if necessary together with the acid catalyst, the resulting mixture, when stirred, turns into a homogeneous solution under formation of various mixed acetals. In some instances, a suspension containing various isomers (e.g. monobenzal, dibenzal, tribenzal) as solids may be formed. In the practice of the invention, such homogeneous solution or suspension is fed to the reaction system.

In preparing said homogeneous solution or suspension, the mole ratio of the polyhydric alcohol to the benzaldehyde compound may be selected within the range of about 1:1 to 1:4. From the viewpoint of improved selectivity toward the compound of general formula (I), however, said ratio should preferably be about 1:1.5 to about 1:3, more preferably about 1:1.8 to about 1:2.2. The lower alcohol is used in an amount of about 0.1 to 5 parts by weight per part by weight of the substrates (i.e. polyhydric alcohol + benzaldehyde compound). The amount of the acid catalyst is not critical provided that the desired effect can be produced. Generally, however, the acid catalyst is used in an amount of about 0.05 to 10 parts by weight, preferably about 0.2 to 3 parts by weight, per 100 parts by weight of the substrates.

The above-mentioned homogeneous solution or suspension can be prepared quickly by merely mixing the substrates with the lower alcohol with stirring in the presence or absence of the acid catalyst, suitably at room temperature or at a temperature in the vicinity of room temperature, either in a separate mixing vessel or in the feed line where a line mixer, for instance, is used.

The hydrophobic organic solvent should preferably have a boiling point within the range of about 40° to 200° C. In particular, benzene, substituted benzenes having 1 to 3 alkyl groups each having 1 to 4 carbon atoms as substituents, such as toluene and xylene, cyclohexane, substitued cyclohexanes having a lower alkyl group of 1 to 4 carbon atoms as substituent, such as methylcyclohexane and ethylcyclohexane, and straight or branched saturated hydrocarbons of 6 to 16, preferably 6 to 12, carbon atoms, such as hexane, heptane, octane, nonane, decane, undecane and dodecane, are preferred because of the ease with which water and the lower alcohol can be removed from the reaction system in the form of an azeotrope therewith.

In accordance with the invention, the above-mentioned homogenous solution or suspension is fed to the reaction system, together with the above-mentioned hydrophobic organic solvent, either continuously or intermittently, at a specific rate, for subjecting the substrates to condensation in the presence of the acid catalyst. The acid catalyst may be added either to the homogeneous solution or suspension in the step of preparing said solution or suspension or to the reaction system via a separate line in the above-specified amount.

Similarly, the hydrophobic organic solvent may be added continuously or intermittently either via the same line as the line for feeding the above-mentioned homogeneous solution or suspension or via a separate line.

As mentioned above, by feeding the above-mentioned homogeneous solution or suspension at a specific rate of feeding, together with the hydrophobic organic solvent, either continuously or intermittently in accordance with the invention, the gelation of the reaction mixture and formation of hard gel particles that would otherwise occur with the progress of the reaction as in the prior art high concentration process can be substantially avoided. In the process according to the invention, the reaction system turns into a slurry or apparently wet powder in about 1 hour after initiation of the reaction as a result of precipitation of crystals of the desired product of general formula (I) as produced. Thereafter, the reaction mixture remains in a slurry or wet powder state even when the material feeding is continued. Therefore, unlike the prior art high concentration process, the process according to the invention does not require any forced agitation device having a kneading or crushing effect. According to the invention, the amount of the homogeneous solution or suspension initially fed is generally very small, and then increases exponentially. Therefore, even if soft gel is formed at the initial stage of the reaction, further feeding of the homogeneous solution or suspension causes the soft gel to become crystalline product. There occurs no rapid increase in load on the impeller blades, and the operation can be conducted in a constant state. Adhesion or deposition of the reactor contents to or on the reactor wall surface is also prevented to a marked extent. Furthermore, the yield of the product can be increased. Since, in the process according to the invention, the substrates are fed in the form of a homogeneous solution or suspension, as mentioned above, the polyhydric alcohol/benzaldehyde mole ratio is maintained constantly within the above-mentioned range during the reaction and accordingly any excessive reaction can be inhibited. As a result, the desired product can be obtained with good selectivity.

In feeding substrates, it is also effective to warm said homogeneous solution or suspension to about 50° to 80° C. to thereby cause a decrease in viscosity of said solution or suspension prior to feeding to the reactor.

The rate of feeding can be suitably selected depending on the reactor capacity. It is rather preferred to increase said rate as the volume of the reactor contents increases than to feed the substrates and so on at a constant rate throughout the reaction period. More specifically, it is advisable to feed said homogeneous solution or suspension to the reactor either continuously or intermittently in a manner such that, on the per-hour basis, about 0.1 to about 2 parts by weight, preferably about 0.3 to about 1 part by weight, of the substrates be fed to the reaction system per part by weight of the compound of general formula (I) present in the reaction system. In the case of intermittent feeding, it is recommendable to add the homogeneous solution or suspension to the reactor at least once hourly, preferably about 2 to 10 times hourly, after initiation of the reaction.

The rate of feeding of the hydrophobic organic solvent should preferably be selected such that the content of the solid (i.e. crystalline precipitate of the compound of general formula (I)) in the reaction system be maintained within the range of about 5 to 90% by weight, more preferably about 20 to 60% by weight. Even when said solid content is outside the above range, no particular difficulties will be encountered. However, when said content is below about 5% by weight, the reaction tends to slow down, whereas, when said content is above about 90% by weight, the selectivity tends to decrease.

Generally, the production process according to the invention is conducted in the following manner. As the reactor, any reactor equipped with a usual agitating mechanism may be used. Preferred, however, are a reversed cone shaped mixer and a horizontal mixer equipped with scraper type agitating blades, for instance. Since little gel formation occurs eventually in the process according to the invention, such forced agitation capable of producing a kneading or crushing effect as required in the prior art high-concentration method is no more necessary. The reactor is preferably equipped with one or more inlets for the above-mentioned homogeneous solution or suspension, hydrophobic organic solvent and so forth, a decanter-equipped condenser, a gas inlet, and so forth. The atmosphere inside the reactor is preferably replaced with an inert gas, such as gaseous nitrogen.

The above reactor is fed with the above-mentioned homogeneous solution or suspension and the hydrophobic organic solvent at the above-mentioned respective rates and the condensation reaction is carried out with stirring. It is recommendable that, in the initial stage, the homogeneous solution or suspension should be fed in small quantities. Thus, for example, about 5 to 10% of the total quantity (volume) of the homogeneous solution or suspension to be eventually fed may preferably be fed as quickly as possible or all at once.

The reaction temperature may vary depending on the substrates, hydrophobic organic solvent and other factors. Generally, however, a temperature of about 40° to 200° C., preferably about 40° to 130° C., is recommendable.

The condensation water formed with the progress of the reaction distills out of the reaction system in the form of an azeotropic mixture with the lower alcohol and hydrophobic organic solvent contained in the reaction mixture of in the manner of gas-liquid equilibrium. The distillate is condensed in the condenser and separated in the decanter into a hydrophobic organic solvent layer and a water-lower alcohol layer. The hydrophobic organic solvent layer may be recycled to the reaction system. The water-lower alcohol layer is taken out of the system.

Although soft gel formation may occur in the initial stage of the reaction, the soft gel formation will not produce any particular trouble since the quantity of the reaction mixture is small in the initial stage of the reaction and since the homogeneous solution or suspension is thereafter fed in a progressively increased amount. The quantity of the reaction mixture increases exponentially as the reaction proceeds. The product of general formula (I) as formed precipitates out as crystals but will not form a gel. Thus, the reaction system, which is liquid or in the form of soft gel in the beginning, quickly becomes a slurry or an apparently wet powder in about 1 hour after initiation of the reaction and, surprisingly, substantially no gelation takes place after that time point if the above-mentioned homogenous solution or suspension and hydrophobic organic solvent are fed continuously or intermittently at rates within the respective ranges specified above. Probably the reaction proceeds on the surface of crystals of the compound of general formula (I) within the reaction system, although no complete understanding of the phenomenon has been gained as yet.

The period starting from initial feeding of the homogeneous solution or suspension to completion of the reaction is generally about 5 to 15 hours and in particular about 6 to 12 hours. After the last feeding operation, stirring should preferably be continued for about 1 to 1.5 hours.

The reaction mixture, which is in the form of a slurry or wet powder, is filtered off if necessary, and then treated in the conventional manner. Thus, the acid catalyst is neutralized with an aqueous solution of an alkali metal hydroxide, and the unreacted substrates (polyhydric alcohol and benzaldehyde compound) and reaction intermediates (monobenzal form, etc.) are washed off with hot water and/or an aqueous surfactant solution. The subsequent drying and grinding or the like treatment give the final product.

In an alternative embodiment of the invention, the reactor may be charged in advance with a certain amount of the acetal of general formula (I) together with an appropriate amount of the hydrophobic organic solvent prior to initiation of the feeding of the homogeneous solution or suspension. In this embodiment, the reaction period can be reduced to about 2 to 6 hours, gel-like substance formation in the reaction mixture can be reduced substantially to nil and, consequently, the yield and purity of the product can be improved.

In this embodiment, a slurry-like or wet powderlike mixture of the compound of general formula (I) and the hydrophobic organic solvent with a solid content of about 5 to 90% by weight, preferably about 30 to 60% by weight, is preferably charged into the reactor in advance. Said mixture may contain about 0.2 to 3 parts by weight of the acid catalyst and/or about 5 to 30 parts by weight of the lower alcohol, per 100 parts by weight of the compound of general formula (I) contained in said mixture. The amount of the compound of general formula (I) contained in said mixture is preferably up to about 50% by weight, more preferably about 5 to 30% by weight, based on the total weight of the compound of the formula (I) contained in said mixture charged in advance plus the amount of the compound of the formula (I) to be produced (assuming that the yield is 100%) from the above-mentioned homogeneous solution or suspension to be fed continuously or intermittently. Since, in this case, the compound of general formula (I) is already present in the reaction system, the above-mentioned homogeneous solution or suspension and the hydrophobic organic solvent can be fed to the reactor continuously or intermittently each at a higher rate as compared with the case in which preliminary feeding of said mixture is not made, whereby the reaction time can be reduced. The reaction mixture obtained can be treated in the same manner as mentioned above to give the desired final product.

The following examples are further illustrative of the present invention.

EXAMPLE 1

A mixture of 20 kg of sorbitol, 27 kg of p-tolualdehyde (p-tolualdehyde/sorbitol mole ratio=2.1) and 27 kg of methanol was heated at 50° C. with stirring in the presence of 0.3 kg of sulfuric acid, to give a homogeneous solution.

A 200-liter reversed cone type (V-shaped) reactor equipped with an agitator and a decanter-equipped condenser was fed with 7 liters of the above homogeneous solution and 9 liters of cyclohexane (via a separate line) within the first 10 minutes, while the reactor contents were agitated at 70° C.

While monitoring continuously the quantity of the product 1,3:2,4-ditoluylidenesorbitol within the reaction system, the above homogeneous solution was fed to the reactor continuously over 4 hours at a rate such that the quantity of the substrates (sorbitol and p-tolualdehyde) fed amounted, on the per-hour basis, to 0.4 part by weight per part by weight of the product 1,3:2,4-ditoluylidenesorbitol as assayed in the reaction system. During this feeding, cyclohexane was fed to the reactor continuously at a rate such that the solid concentration within the reaction system remained at a level of 35% by weight.

Throughout the reaction period (6 hours from initiation of feeding), the reaction mixture was heated at a temperature of 65° to 75° C. while the byproduct water, methanol and cyclohexane were distilled off as an azeotrope. The cyclohexane in the distillate was separated in the decanter and recycled to the reaction system. The water-methanol layer was removed from the reaction system.

At 2 hours after initiation of the reaction and thereafter, the conversion and selectivity of the desired product 1,3:2,4-ditoluylidenesorbitol were always not less than 90% based on the total amount of the substrates already fed. The reaction mixture obtained at 5 hours after initiation of the reaction was neutralized, washed with water and dried in the conventional manner to give the desired product in a 99.5% purity and a 93% yield.

EXAMPLE 2

The procedure of Example 1 was followed using benzaldehyde as the aromatic aldehyde. Dibenzylidenesorbitol was obtained in 99% purity and 90% yield.

EXAMPLE 3

The procedure of Example 1 was followed using p-ethylbenzaldehyde as the aromatic aldehyde. Bis(p-ethylbenzylidene)sorbitol was obtained in 98% purity and 95% yield.

EXAMPLE 4

The procedure of Example 1 was followed using p-chlorobenzaldehyde as the aromatic aldehyde. Bis(p-chlorobenzylidene)sorbitol was obtained in 97.5% purity and 95% yield.

COMPARATIVE EXAMPLE 1

The reactor used in Example 1 was charged with the whole amount of the reactant mixture (homogeneous solution) all at once and the reaction was carried out under the same temperature and agitation conditions as in Example 1. In about 1 hour, the reaction system became gel-like and in a short time thereafter the load on the impeller blades became excessive, so that the reaction had to be discontinued.

EXAMPLE 5

A mixture of 20 kg of sorbitol, 27 kg of p-tolualdehyde and 30 kg of methanol was stirred at 40° C. in the presence of p-toluenesulfonic acid to give a homogeneous solution.

A 200-liter reversed cone shaped reactor equipped with an agitator and a condenser with a decanter was preliminarily charged with 4 kg of di(p-toluylidene)sorbitol, 4 kg of cyclohexane, 40 g of p-toluenesulfonic acid and 1 kg of methanol and the reactor contents were stirred at room temperature to give a wet powder.

To the reactor was then fed the above homogeneous solution continuously at a rate such that the substrates in said solution amounted to 0.3 part by weight per part by weight of the di(p-toluylidene)sorbitol within the reaction system on the per-hour basis. Through a separate line, cyclohexane was simultaneously fed to the reactor continuously at a rate such that the solid concentration within the reaction system could remain at a level of 50% by weight.

The reaction was carried out at 70° to 75° C. with stirring for 6 hours while an azeotropic mixture consisting of the byproduct water, methanol and cyclohexane was distilled off. The cyclohexane separated in the decanter was recycled to the reaction system, and water-methanol layer was taken out of the reaction system.

The reaction mixture obtained was worked up in the same manner as in Example 1 to give 99.5% pure di(p-toluylidene)sorbitol in a 95% yield.

What is claimed is:

1. A process for batchwise production of an acetal of the general formula

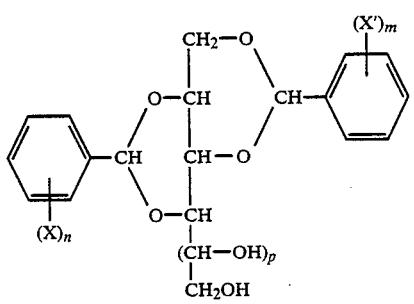

wherein X and X' are the same or different and each represent a hydrogen or halogen atom, an alkyl or alkoxy group containing 1 to 4 carbon atoms or a carboxyl group, m and n each represent an integer of 1 to 5 and p is 0 (zero) or 1, which comprises subjecting (a) a polyhydric alcohol of the general formula

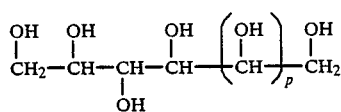

wherein p is as defined above, and (b) a benzaldehyde compound of the general formula

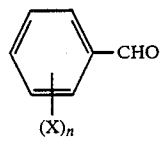

wherein X and n are as defined above, or a benzaldehyde compound of the general formula

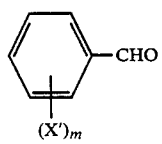

wherein X' and m are as defined above, or a mixture of said compound of general formula (III) and said compound of general formula (IV), to condensation reaction in a reactor by feeding a homogeneous solution or suspension containing (a) said polyhydric alcohol of general formula (II),
(b) said compound of general formula (III) or (IV) or said mixture,
(c) a lower alcohol and, optionally,
(d) an acid catalyst, to the reactor, together with a hydrophobic organic solvent, continuously or intermittently while adjusting the rate of feeding of said homogeneous solution or suspension such that said polyhydric alcohol of general formula (II) and said compound of general formula (III) or (IV) or said mixture are fed to the reaction system in a total amount per hour of about 0.1 to about 2 parts by weight per part by weight of the acetal of general formula (I) as found in the reaction system.

2. A process as claimed in claim 1, wherein the rate of feeding of said homogeneous solution or suspension is adjusted such that said polyhydric alcohol of general formula (II) and said compound of general formula (III) or (IV) or said mixture are fed to the reaction system in a total amount per hour of about 0.3 to about 1 part by weight per part by weight of the acetal of general formula (I) as found in the reaction system.

3. A process as claimed in claim 1, wherein said hydrophobic organic solvent is fed to the reactor continuously or intermittently at a rate such that the solid content within the reaction system can be maintained at 5 to 90% by weight.

4. A process as claimed in claim 1, wherein said hydrophobic organic solvent is fed to the reactor continuously or intermittently at a rate such that the solid content within the reaction system can be maintained at about 20 to about 60% by weight.

5. A process as claimed in claim 1, wherein the mole ratio of said polyhydric alcohol of general formula (II) to said compound of general formula (III) or (IV) or said mixture in said homogeneous solution or suspension is about 1:1 to about 1:4.

6. A process as claimed in claim 5, wherein said mole ration is about 1:1.5 to about 1:3.

7. A process as claimed in claim 5, wherein said mole ratio is about 1:1.8 to about 1:2.2.

8. A process as claimed in claim 1, wherein the lower alcohol is used in an amount of about 0.1 to about 5 parts by weight per part by weight of the amount of the polyhydric alcohol of general formula (II) and the compound of general formula (III) or (IV) or said mixture.

9. A process as claimed in claim 1, wherein the acid catalyst is used in an amount of about 0.05 to about 10 parts by weight per 100 parts by weight of the amount of the polyhydric alcohol of general formula (II) and the compound of general formula (III) or (IV) or said mixture.

10. A process as defined in claim 1, wherein the acid catalyst is used in an amount of about 0.2 to about 3 parts by weight per 100 parts by weight of the amount of the polyhydric alcohol of general formula (II) and the compound of general formula (III) or (IV) or said mixture.

11. A process as defined in claim 1, wherein the condensation reaction is conducted at about 40° to about 200° C.

12. A process as defined in claim 1, wherein the condensation reaction is conducted at about 40° to about 130° C.

13. A process as claimed in claim 1, wherein the reactor is charged in advance with a mixture containing said acetal of general formula (I) and a hydrophobic organic solvent and having a solid content of 5 to 90% by weight.

14. A process as claimed in claim 13, wherein said mixture further contains about 0.2 to 3 parts by weight of an acid catalyst and about 5 to 30 parts by weight of a lower alcohol, per 100 parts by weight of said acetal of general formula (I) contained in said mixture.

15. A process as claimed in claim 1, wherein the condensation reaction is conducted while removing the resulting condensation water from the reaction system in the form of an azeotropic mixture with the lower alcohol and hydrophobic organic solvent or according to gas-liquid equilibrium.

* * * * *